(12) United States Patent
Strong et al.

(10) Patent No.: US 6,830,573 B2
(45) Date of Patent: Dec. 14, 2004

(54) SURGICAL FASTENER SYSTEM

(75) Inventors: J. Todd Strong, Birmingham, AL (US); Rickey D. Hart, Plainville, MA (US); R. Steven Boggan, Hoover, AL (US); Prasad V. Nalluri, Jacksonville, FL (US)

(73) Assignee: Biohorizons Implant Systems, Inc., Birmingham, AL (US)

( * ) Notice: Subject to any disclaimer, the term of this patent is extended or adjusted under 35 U.S.C. 154(b) by 57 days.

(21) Appl. No.: 10/132,608

(22) Filed: Apr. 25, 2002

(65) Prior Publication Data

US 2002/0121539 A1 Sep. 5, 2002

Related U.S. Application Data

(63) Continuation of application No. 09/458,914, filed on Dec. 10, 1999, now Pat. No. 6,402,759.
(60) Provisional application No. 60/111,828, filed on Dec. 11, 1998.

(51) Int. Cl.[7] .............................................. A61B 17/56
(52) U.S. Cl. ......................................... 606/73; 206/343
(58) Field of Search ............................ 606/73, 99, 100, 606/104; 81/44, 413; 227/175.1; 206/343–346, 820; 411/422, 443

(56) References Cited

U.S. PATENT DOCUMENTS

| | | | | |
|---|---|---|---|---|
| 3,010,193 A | | 11/1961 | Croall, Jr. et al. ............ 29/278 |
| 3,661,251 A | * | 5/1972 | Waeltz ........................ 206/346 |
| 3,915,299 A | * | 10/1975 | Miyaoku ..................... 206/345 |
| 3,927,459 A | * | 12/1975 | Haytayan ..................... 29/413 |
| 4,106,619 A | * | 8/1978 | Haytayan .................... 206/346 |
| 4,222,304 A | * | 9/1980 | Yoshida et al. ............... 411/34 |
| 4,586,607 A | * | 5/1986 | Dubbs et al. ............... 206/716 |
| 5,080,229 A | * | 1/1992 | Adkins et al. .............. 206/343 |
| 5,398,861 A | * | 3/1995 | Green ..................... 227/175.1 |
| 5,741,268 A | | 4/1998 | Schütz ....................... 606/104 |
| 5,823,338 A | * | 10/1998 | Osterle et al. .............. 206/338 |
| 5,921,736 A | * | 7/1999 | Habermehl ................. 411/442 |
| 5,928,244 A | | 7/1999 | Tovey et al. ................ 606/104 |
| 6,273,893 B1 | | 8/2001 | McAllen, III et al. ...... 606/104 |
| 6,551,343 B1 | * | 4/2003 | Tormala et al. ............. 606/213 |

* cited by examiner

*Primary Examiner*—Kevin Shaver
*Assistant Examiner*—D. Austin Bonderer
(74) *Attorney, Agent, or Firm*—Needle & Rosenberg, P.C.

(57) ABSTRACT

A surgical fastener system is disclosed. The system includes a surgical fastener, a surgical fastener holder sized and shaped to receive the surgical fastener at least partially therein, and a surgical fastener driver having a seat sized and shaped to frictionally receive a head of the surgical fastener therein. The fastener driver is constructed and arranged to selectively urge the fastener, and more particularly the fastener head, out of the seat. The surgical fastener driver thus includes an elongate body with the seat defined at an end thereof, and a drive piston disposed within the body. The drive piston has a first retracted position, and a second extended position in which at least a portion of the piston extends into the seat to urge the fastener out of the seat during usage. Also disclosed is a surgical fastener and a surgical fastener holder, respectively, for use with the system.

39 Claims, 2 Drawing Sheets

SURGICAL FASTENER SYSTEM

CROSS-REFERENCE TO RELATED APPLICATIONS

This patent application claims priority to U.S. Provisional Patent Application Ser. No. 60/111,828, filed on Dec. 11, 1998, and is a continuation application of U.S. patent application Ser. No. 09/458,914 now U.S. Pat. No. 6,402, 759, filed on Dec. 10, 1999, respectively, in the United States Patent and Trademark Office.

FIELD OF THE INVENTION

The invention relates to medical devices generally, and more particularly to systems for applying surgical fasteners that secure membranes to biological tissues such as bone.

BACKGROUND OF THE INVENTION

In surgery, for example reconstructive oral or dental surgery, when grafting bone a membrane is placed over the bone to allow the bone to regrow without contamination. The membrane is typically fastened to the bone using screws or hand-driven tacks. Because the screws used are small, and therefore hard to drive into bone, they currently are rarely used in oral surgery.

Hand driven tacks are more commonly used. In use, the tacks are held by a pick up tool and driven into position with a mallet. The tacks may also be pushed into position by hand. The tools employed with tacks, however, tend to be bulky and, given that the tacks used tend to be small, the tacks are hard to handle.

There is a need, therefore, for a surgical fastener system that facilitates the handling and use of tissue tacks in dental surgery

SUMMARY OF THE INVENTION

One aspect of the invention is a surgical fastener driver having a handle and a tube extending therefrom. The handle defines a cavity therein. The tube is in communication with the cavity and is affixed to the handle. The tube extends outwardly from the cavity to a seat, which is shaped so as to receive a surgical fastener therein. A piston, having an outward end, is disposed within the tube and extends from the cavity to the seat. The piston has a retracted position in which the outward end does not extend into the seat, and an extended position in which the outward end extends into the seat.

A trigger is integrated with the handle of the fastener driver, and has a first state in which the piston is held in the retracted position, and a second state in which the piston is released so as to allow the piston to move to the extended position. A driver is disposed within the cavity and exerts an outward force on the piston in order to drive the piston into the extended position when the trigger is moved into its second state.

In another aspect, the invention is a surgical fastener for securing surgical membrane materials to body tissues (such as bone). The fastener includes a tack that includes an elongate stem having a proximal end and a distal end, a head disposed at the proximal end of the stem, and a plurality of discrete axially spaced annular ribs disposed in successive longitudinal positions along the stem. The head has a diameter sized to frictionally fit within the seat of a delivery device, which may include, for example, the surgical fastener driver described above.

In yet another aspect, the invention is a holder for surgical fasteners that includes a first block and a second block. The first block has a top surface and defines a plurality of cavities opening to the top surface, wherein each cavity is shaped so as to be capable of receiving a tack therein. The second block has an upper surface and an opposite lower surface complementary in shape to the top surface of the first block. The second block defines a plurality of holes passing from the upper surface to the lower surface, each of which is in alignment with a corresponding cavity in the first block when the lower surface of the second block is placed against the top surface of the first block. A loading pin is disposed within a selected one of the plurality of cavities through at least a portion of the corresponding hole.

These and other aspects of the invention will become apparent from the following description of the preferred embodiment taken in conjunction with the following drawings, although variations and modifications may be effected without departing from the spirit and scope of the novel concepts of the disclosure.

DETAILED DESCRIPTION

Figure 1A:
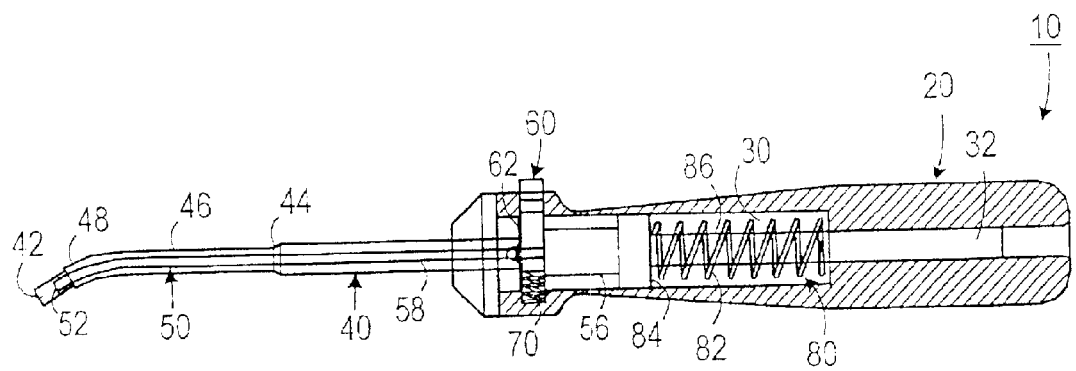
FIG. 1A is a schematic illustration of a surgical fastener driver of the present invention.

A preferred embodiment of the invention is now described in detail. Referring to the drawings, like numbers indicate like parts throughout the several views. As used in the description herein and throughout the claims that follow, the words "a," "an," and "the" includes plural reference unless the context clearly dictates otherwise. Also, as used in the description herein and throughout the claims that follow, the meaning of "in" includes "in" and "on" unless the context clearly dictates otherwise. Also, "complimentary in shape" means having generally compatible dimensions, without necessarily having an identical shape.

As shown in FIGS. 1A–1D, the surgical fastener driver 10, according to one illustrative embodiment of the invention, includes a handle 20 that defines a cavity 30. The cavity 30 is cylindrical and has a smaller elongate alignment cavity 32 defined therein and extending axially away therefrom. The handle 20 may be machined from a metal, such as aluminum, stainless steel, or any desired one of the many metals typically used in the manufacture of medical instruments, or from other materials generally known in the art. A tube 40 extends from the cavity 30 and is affixed to the handle 20. The hollow core of the tube 40 is in communication with the cavity 30. The tube 40 ends in a seat 42 that is sized and shaped to receive a surgical fastener 102 therein. The tube 40 may be strengthened without increasing its bulk near the seat 42 by including a taper 44, thereby allowing for the use of narrower tubing near the seat 42. The tube also includes a first section 46 and a second section 48. The second section 48 deflects at an angle away from the first section 46 to facilitate the placement of surgical fasteners in hard to reach areas.

Figure 1B:
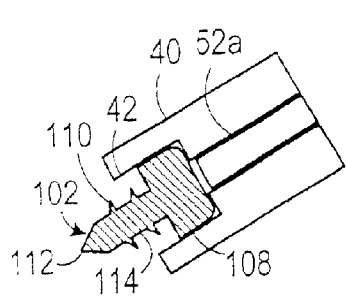
FIG. 1B is an enlarged partial schematic view of a surgical fastener positioned within a seat defined at an end of the surgical fastener driver of FIG. 1A, with an outward end of a driver piston shown in a retracted position.
Figure 1C:
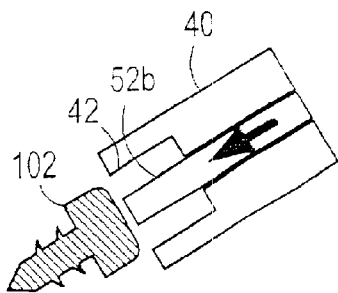
FIG. 1C is an enlarged partial schematic view of the seat of the surgical fastener driver of FIG. 1A with the outward end of the driver piston shown in an extended position.
Figure 1D:
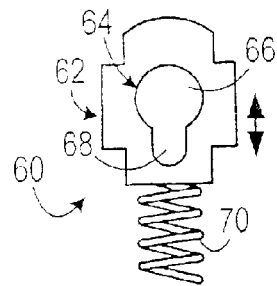
FIG. 1D is an elevational view of a trigger assembly for use with the surgical fastener driver of FIG. 1A.

Referring now to FIG. 1A, a piston 50, having a first elongate portion 58 terminating in an outward end 52, is disposed within the tube 40 and extends from the cavity 30 to the seat 42. The piston 50 as constructed has the first elongate portion 58, and a second portion 56. As illustrated, the cross-section of the second portion 56 is greater than the cross section of the first portion 58. As illustrated in FIG. 1B, the piston 50 has a retracted position in which the outward end 52a thereof does not extend into the seat 42, so that a surgical fastener 102 may be held in the seat 42. As illustrated in FIG. 1C, the piston 50 also has an extended position in which the outward end 52b thereof extends into the seat 42. When the piston 50 is forced into the extended position, the surgical fastener 102 is thus forced out of the seat 42. Accordingly, should the seat 42 be placed against a membrane (not illustrated), the surgical fastener 102 is forced into the membrane, thereby fastening it to the underlying bone (not illustrated) in the patient's mouth.

The fastener driver also has a trigger 60 integrated with the handle 20. The trigger 60 has a first state in which the piston 50 is held in the retracted position (FIG. 1A) and a second state in which the piston 50 is released so as to be allowed to move into its extended position (FIG. 1B). As shown in detail in FIG. 1D, the trigger 60 includes a locking member plate 62 that defines a hole 64 passing therethrough. The hole 64 includes a small portion 68 that allows the first elongate portion 58 of the piston 50 to pass therethrough, but prevents the second portion 56 of the piston from passing therethrough, i.e., the small portion holds the piston within the cavity 30 in the piston's retracted position. The small portion 68 thus restricts the piston 50 when the plate 62 is in a first position corresponding to the first state of the trigger 60. The hole 64 also has a large portion 66 that allows both the first portion 58 and the second portion 56 of the piston to pass therethrough when the plate 62 is in a second position corresponding to the second state of the trigger 60. The trigger 60 also includes a second spring 70 that maintains the locking member plate 62 in the first position until it is pushed down, thereby releasing the piston 50.

A driver 80 adapted to exert an outward force on the piston 50 is disposed within the cavity 30 as illustrated. The driver 80 drives the piston 50 into its extended position when the trigger 60 is moved into its second state. As shown in the illustrative embodiment, the driver 80 includes a spring 82 that applies force to a plunger head 84 that caps one end of a plunger cylinder 86. The plunger head 84 has dimensions complimentary to that of the cavity 30 so as to be able to slide back and forth within the cavity 30. The rod of the plunger cylinder 86 fits within the elongate alignment cavity 32 to maintain the alignment of the plunger head 84 within the cavity 30. The spring 82 applies force on the plunger head 84, which in turn applies force to the piston 50, thereby causing the piston 50 to force the surgical fastener 102 into the patient's tissue (not illustrated) when the trigger 60 is actuated to release the piston 50.

As shown in detail in FIG. 1B, one example of a surgical fastener 102 adapted for securing surgical membrane materials to body tissues is a tack that includes an elongate stem 114 having a proximal end and spaced distal end. The tack could comprise, for example, a bio-absorbable material (such as PLLA) or a medical grade metal. A head 108 is disposed at the proximal end of the surgical fastener, or tack, and the distal end terminates at a point 112. A plurality of discrete axially spaced annular ribs 110 is disposed in successive longitudinal positions along the stem 114. The head 108 has a diameter sized to frictionally fit within the seat 42 of the delivery device 10, i.e., the fastener driver.

Figure 2A:
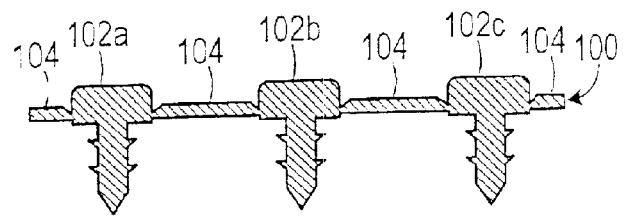
FIG. 2A is a cross sectioned elevational view of a plurality of surgical fasteners or tacks connected to one another by a common runner.
Figure 2B:
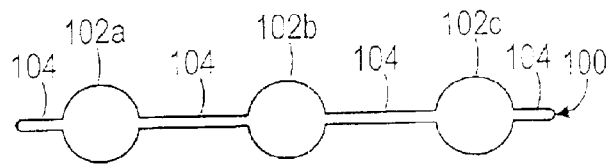
FIG. 2B is a top plan view of the surgical fasteners of FIG. 2A.
Figure 3A:
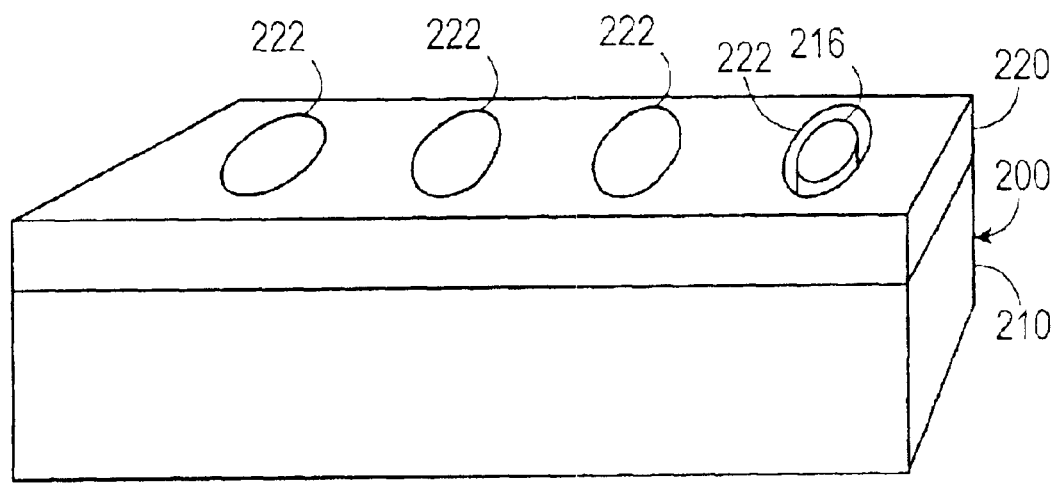
FIG. 3A is a perspective view of a surgical fastener holder of the present invention.
Figure 3B:
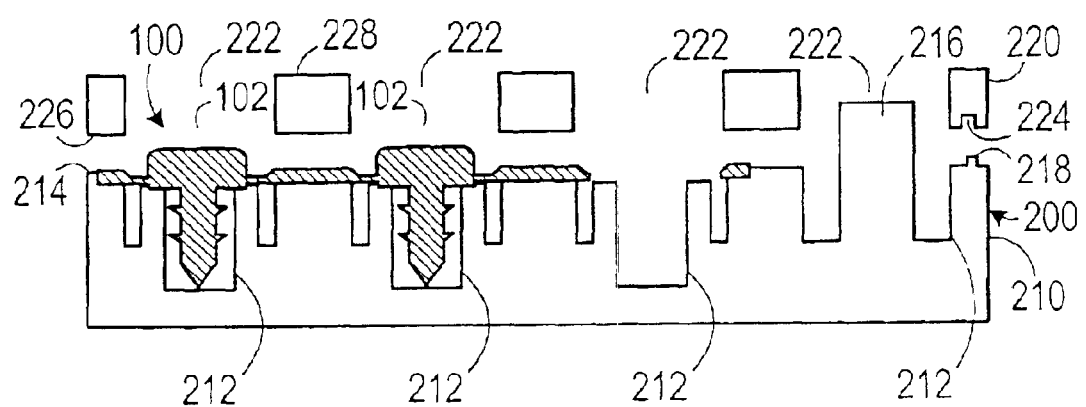
FIG. 3B is a cross sectioned elevational view of the holder of FIG. 3A.

As shown in FIGS. 2A and 2B, a tack strip 100 may be formed of a plurality of fasteners 102a–c connected to one another by an integrally formed linear runner 104. Such a tack strip 100 would facilitate ease of use with a surgical fastener holder 200, as shown in FIGS. 3A and 3B.

The holder 200 includes a first block 210 and a second block 220. The first block 210 has a top surface 214 within which a plurality of cavities 212 are defined. Each cavity 212 is sized to be capable of receiving a tack therein. The second block 220 has an upper surface 228 and a spaced opposite lower surface 226 which is complementary in shape to the top surface 214 of the first block 210. The second block 220 defines a plurality of holes 222 passing therethrough so that each of the plurality of holes 222 is in alignment with a corresponding cavity 212 in the first block 210 when the lower surface 226 of the second block 220 is placed against the top surface 214 of the first block 210. A loading pin 216, for use with the fastener driver, as described in greater detail below, is disposed within a selected one of the plurality of cavities 212 and extends through at least a portion of the corresponding hole 222.

If the holder 200 is to be reusable, both the first block 210 and the second block 220 should comprise a material able to withstand standard sterilization techniques (such as exposure to high temperature or radiation). For example, in one embodiment, metal is used to construct the holder. If the holder 200 is to be disposable, then one of many materials known to those of skill in the art could be used (e.g., polycarbonate).

To facilitate the alignment and securing of the first block 210 to the second block 220, one or more pins 218 (FIG. 3B) may be added to extend from the top surface 214 of the first block 210 and one or more holes 224 (FIG. 3B) may be defined within the lower surface 226 of the second block 220. Each hole 224 is complementary in shape to, and in alignment with, a selected (corresponding) pin 218. As is readily understood, the pins 218 could extend from the second block 220 while the holes extend into the first block 210 without departing from the scope of the invention.

Referring now to FIGS. 1A–3B, in use the tack strip 100 is placed within or on the first block 210 of the holder 200, as illustrated, so that the individual surgical fasteners or tacks 102 extend into and fit within the respective cavities 212. The second block 220 is then secured to the first block 210 as described above. The operator then prepares the fastener driver 10 for use by forcing the outward end 52 of the piston 50 down onto the loading pin 216 which will, in turn, force the piston 50 back into the cavity 30 until the trigger 60 locks the piston into its retracted position. The seat 42 is then placed over one of the available surgical fasteners 102 in the holder 200 and pushed down until the selected surgical fastener 102 breaks away from the runner 104 and fits frictionally within the seat 42 (FIG. 1B). The seat 42 is then placed against the membrane (not illustrated) to be fastened, the locking member plate 62 is pressed down to release the piston 50 from its retracted position, and the surgical fastener 102 is forced by the piston into and through the membrane and the into the tissue (not illustrated) to which the membrane is to be fastened.

The embodiments described herein are presented as illustrative examples only, and are not intended to impose any limitations on the invention. It will be readily appreciated by those skilled in the art that many alternate embodiments may be made from the specific embodiments disclosed in this specification without departing from the invention. Accordingly the described embodiments are intended to cover all such modifications coming within the anticipated scope of this invention.

We claim:

1. A surgical fastener system, said system comprising:
   a surgical fastener, the fastener having an elongate body with a head formed at one end thereof;
   a surgical fastener holder sized and shaped to receive the surgical fastener at least partially therein, the surgical fastener holder having a first block having a top surface in which at least one cavity is defined, the at least one cavity being sized and shaped to receive at least a portion of the surgical fastener therein; and
   a surgical fastener driver having a seat sized and shaped to frictionally receive the head of the surgical fastener therein.

2. The surgical fastener system of claim 1, the surgical fastener driver being constructed and arranged to selectively urge the fastener out of the seat.

3. The surgical fastener system of claim 1, the surgical fastener driver further comprising:
   an elongate body, the seat being defined at an end thereof; and
   a drive piston disposed within said body;
   the drive piston having a first retracted position, and a second extended position in which at least a portion of the piston extends into the seat to urge the fastener out of the seat.

4. The surgical fastener system of claim 3, the surgical fastener driver further comprising:
   a drive spring disposed within said body and being operably coupled with said drive piston; and
   a trigger assembly;
   the drive piston being urged against the drive spring within said first retracted position and held therein by the trigger assembly, the drive piston being biased by the drive spring into said second extended position in response to the actuation of the trigger assembly.

5. The surgical fastener system of claim 4, wherein the drive spring is compressed when the drive piston is in the first retracted position.

6. The surgical fastener system of claim 4, wherein the trigger assembly comprises a locking member that selectively holds the drive piston in the first retracted position.

7. The surgical fastener system of claim 6, the trigger assembly further comprising a spring operably coupled with said locking member, the trigger assembly having a spring loaded locked position and a release position in which the drive piston is released by the trigger assembly to move into its second extended position.

8. The surgical fastener system of claim 1, the body of the surgical fastener comprising an elongate stem having a proximal end and a spaced distal end, the head being formed at the proximal end of the stem and being sized and shaped to be frictionally received within the seat of the surgical fastener driver and held therein.

9. The surgical fastener system of claim 8, further comprising a series of annular ribs formed on and projecting outwardly of the stem, the ribs being spaced from one another in the lengthwise direction of the stem.

10. The surgical fastener system of claim 1, further comprising a plurality of the surgical fasteners connected in series with one another by an elongate runner.

11. The surgical fastener system of claim 10, the runner being formed with and as a part of the series of fasteners.

12. The surgical fastener system of claim 10, wherein the elongate runner is received on the top surface of the first block and is sandwiched between the first block and the second block, respectively, of the holder once the two blocks are joined to one another.

13. The surgical fastener system of claim 12, wherein the elongate runner is received on the top surface of the first block so that each respective surgical fastener of the plurality of surgical fasteners is at least partially received within a respective one of the cavities defined in the first block, and so that each respective surgical fastener of the plurality of surgical fasteners is at least partially extended within a respective one of the corresponding holes defined in the second block once the two blocks are joined to one another.

14. The surgical fastener system of claim 1, the surgical fastener being comprised of a medical grade metal.

15. The surgical fastener system of claim 1, the surgical fastener being comprised of a bio-absorbable material.

16. The surgical fastener system of claim 1, the second block further comprising a loading pin disposed within a cavity of the first block and extended at least partially through a corresponding hole within the second block.

17. The surgical fastener system of claim 16, wherein the seat of the surgical fastener driver is sized and shaped to be passed over the loading pin.

18. The surgical fastener system of claim 17, the surgical fastener driver comprising:
   an elongate body, the seat being defined at an end thereof;
   a drive piston disposed within said body; and
   a drive spring disposed within said body and being operably coupled with said drive piston;
   the drive piston having a first retracted position, and a second extended position in which at least a portion of the piston extends into the seat to urge the fastener out of the seat.

19. The surgical fastener system of claim 18, wherein the at least a portion of the drive piston extended into the seat is urged against the loading pin as the seat of the surgical fastener driver is passed over and down onto the loading pin so that the loading pin in turn urges the at least a portion of the drive piston against the drive spring to move the drive piston into a retracted position with respect to the seat of the surgical fastener driver.

20. The surgical fastener system of claim 1, the bolder for the surgical fastener further comprising a second block having an upper surface and a spaced lower surface, the lower surface being complementary in shape to the top surface of the first block, the second block defining at least one hole therein and extending therethrougb, the at least one hole being in alignment with a corresponding cavity in the first block when the second block is placed on the first block in overlying registration.

21. A surgical fastener holder for use with a surgical fastener system having at least one surgical fastener and a surgical fastener driver provided with a seat sized and shaped to frictionally receive a head of the surgical fastener therein, said, surgical fastener holder comprising:
   a first block having a top surface in which a first cavity is defined, the first cavity being sized and shaped to receive at least a portion of the at least one surgical fastener therein; and a second block having an upper surface and a spaced lower surface, the lower surface being complementary in shape to the top surface of the first block, the second block defining a first hole therein and extending therethough, the first hole being in alignment with the corresponding first cavity in the first block when the second block is placed on the first block.

22. The surgical fastener holder of claim 21, the second block further comprising a loading pin disposed within a second cavity of the first block and extended at least partially through a corresponding second hole defined within the second block.

23. The surgical fastener holder of claim 21, wherein the loading pin is sized and shaped to be received with the seat of the surgical fastener driver.

24. The surgical fastener holder of claim 21, the first block having a plurality of cavities defined therein, wherein each said cavity opens to the top surface of the first block and is sized and shaped to receive at least a portion of the at least one surgical fastener therein, the second block having a plurality of holes defined therein and extending therethrough, each respective hole of the plurality of holes being in alignment with a corresponding cavity in the first block when the lower surface of the second block is placed on the top surface of the first block.

25. The surgical fastener holder of claim 21, the first block and the second block each being formed of a plastic material.

26. The surgical fastener holder of claim 21, the first block and the second block each being fanned of a metallic material.

27. The surgical fastener holder of claim 21, further comprising at least one elongate indexing pin extended from the top surface of the first black and at least one indexing hole defined within the lower surface of the second black, the at least one pin being sized and shaped to be received within the at least one hole.

28. The surgical fastener holder of claim 27, wherein the at least one cavity of the first block is aligned with the at least one hole of the second block when the at least one indexing pin of the first block is received within the at least one indexing hole of the second block.

29. A surgical fastener system, said system comprising:
   a surgical fastener, the surgical fastener having an elongate body with a head formed at one end thereof;
   a surgical fastener holder comprising:
      a first block having a top surface in which at least one cavity is defined, the at least one cavity being sized and shaped to receive at least a portion of the surgical fastener therein, and
      a second block having an upper surface and a spaced lower surface, the lower surface being complementary in shape to the top surface of the first block, the second block defining at least one hole therein and extending therethrough, the at least one hole being in alignment with a corresponding cavity in the first block when the second block is placed on the first block; and
   a surgical fastener driver comprising:
      an elongate body having a seat sized and shaped to frictionally receive the head of the surgical fastener therein being defined at an end thereof, and
      a drive piston disposed within said body, the drive piston having a first retracted position, and a second extended position in which at least a portion of the piston extends into the seat to urge the fastener out of the seat.

30. The surgical fastener system of claim 29, the body of the surgical fastener comprising an elongate stem having a proximal end and a spaced distal end, the head being formed at the proximal end of the stem and being sized and shaped to be frictionally received within the seat of the surgical fastener driver and held therein.

31. The surgical fastener system of claim 30, further comprising a series of annular ribs formed on and projecting outwardly of the stem, the ribs being spaced from one another in the lengthwise direction of the stem.

32. The surgical fastener system of claim 30, further comprising a plurality of the surgical fasteners connected in series with one another by an elongate runner.

33. The surgical fastener system of claim 32, the runner being formed with and as a part of the series of fasteners.

34. The surgical fastener system of claim 29, the surgical fastener being comprised of a medical grade metal.

35. The surgical fastener system of claim 29, the surgical fastener being comprised of a bio-absorbable material.

36. The surgical fastener system of claim 29, the second block further comprising a loading pin disposed within a cavity of the first block and extended at least partially through a corresponding hole within the second block.

37. The surgical fastener system of claim 36, wherein the seat of the surgical fastener driver is sized and shaped to be passed over the loading pin.

38. The surgical fastener system of claim 37, the surgical fastener driver further comprising:
   a drive spring disposed within said body and being operably coupled with said drive piston; and
   a trigger assembly;
   the drive piston being urged against the drive spring within said first retracted position and held therein by the trigger assembly, the drive piston being biased by the drive spring into said second extended position in response to the actuation of the trigger assembly, wherein the at least a portion of the drive piston extended into the seat is urged against the loading pin of the second block of the surgical fastener holder as the seat of the surgical fastener driver is passed over and down onto the loading pin so that the loading pin in turn urges the at least a portion of the drive piston against the drive spring to move the drive piston into a retracted position with respect to the seat of the surgical fastener driver.

39. The surgical fastener system of claim 29, the surgical fastener driver further comprising:
   a drive spring disposed within said body and being operably coupled with said drive piston; and
   a trigger assembly; the drive piston being urged against the drive spring within said first retracted position and held therein by the trigger assembly, the drive piston being biased by the drive spring into said second extended position in response to the actuation of the trigger assembly.

* * * * *